US00PP33538P2

(12) United States Plant Patent
Welzel

(10) Patent No.: US PP33,538 P2
(45) Date of Patent: Oct. 5, 2021

(54) POINSETTIA PLANT NAMED 'WEL20390'

(50) Latin Name: *Euphorbia pulcherrima*
Varietal Denomination: WEL20390

(71) Applicant: Christian Welzel, Kerken (DE)

(72) Inventor: Christian Welzel, Kerken (DE)

( * ) Notice: Subject to any disclaimer, the term of this patent is extended or adjusted under 35 U.S.C. 154(b) by 0 days.

(21) Appl. No.: 17/148,243

(22) Filed: Jan. 13, 2021

(51) Int. Cl.
*A01H 5/02* (2018.01)
*A01H 6/38* (2018.01)

(52) U.S. Cl.
USPC ..... Plt./303

(58) Field of Classification Search
USPC ..... Plt./303, 307
See application file for complete search history.

*Primary Examiner* — Annette H Para
(74) *Attorney, Agent, or Firm* — Weatherly IP Solutions, LLC; James M. Weatherly

(57) ABSTRACT

A new poinsettia plant particularly distinguished by having red bracts with large white spots, with more variance in spot size and an earlier appearance of the spots, is disclosed.

1 Drawing Sheet

Genus and species: *Euphorbia puicherrima.*
Variety denomination: 'WEL20390'.

BACKGROUND OF THE NEW PLANT

The present invention comprises a new and distinct variety of poinsettia, botanically known as *Euphorbia puicherrima* and hereinafter referred to by the variety name 'WEL20390'. 'WEL20390' was discovered in November 2018 as a branch mutation from the poinsettia plant 'WEL19375' (U.S. Plant Pat. No. 31,759) in Kerken, Germany.

In December 2018, vegetative cuttings of the mutation plant 'WEL20390' were first propagated in Kerken, Germany. 'WEL20390' was found to reproduce true to type in successive generations of asexual propagation via vegetative cuttings in Kerken, Germany.

SUMMARY

The following are the most outstanding and distinguishing characteristics of this new variety when grown under normal horticultural practices in Stuttgart, Germany.

1. Red bracts with white spots;
2. Larger white spots on the bracts;
3. More variance in spot size on the bracts; and
4. An earlier appearance of the spots.

DESCRIPTION OF THE PHOTOGRAPH

This new poinsettia plant is illustrated by the accompanying photograph which shows an overall view of the plant. The photograph is of a plant approximately twelve-weeks-old grown indoors Stuttgart, Germany in December 2020. The colors shown are as true as can be reasonably obtained by conventional photographic procedures.

DESCRIPTION OF THE NEW VARIETY

The following detailed descriptions set forth the distinctive characteristics of 'WEL20390'. The data which define these characteristics were collected from asexual reproductions carried out in Stuttgart, Germany. Data was collected on plants 20 weeks from potting, grown indoors in Stuttgart, Germany under greenhouse conditions in December of 2020. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'WEL20390'.

Parentage:
- *Male.*—None.
- *Female.*—Branch mutation from the commercial variety 'WEL19375' (U.S. Plant Pat. No. 31,759).

Plant:
- *Form.*—Triangular.
- *Growth habit.*—Upright.
- *Height.*—23.0 cm to 25.0 cm.
- *Width.*—28.0 cm to 35.0 cm.
- *Average number of inflorescences per plant.*—5 to 6.
- *Keeping quality.*—Very good.
- *Blooming habit.*—Intermittent.
- *Flowering response time.*—Approximately 56 days.
- *Disease and pest resistance.*—None observed.

Propagation:
- *Type cuttings.*—Apical cuttings.
- *Time to produce a rooted cutting.*—4 weeks.
- *Rooting habit and root color.*—Freely branching and white.

Lateral branches:
- *Color.*—Close to RHS N138B on lower quarter and close to RHS 59A on upper three quarters.
- *Length.*—20.0 cm to 22.0 cm.
- *Internode length.*—1.5 cm to 4.0 cm.
- *Diameter.*—0.5 cm to 0.8 cm.
- *Branching habit.*—Freely branching.
- *Number of lateral branches per plant.*—5 to 6.
- *Texture.*—Smooth.

Leaves:
- *Quantity.*—5 to 6 per lateral branch.

*Arrangement.*—Alternate.
*Number of lobes on the leaf blade.*—0 to 3 (please note that more than 95% of the leaves have no lobes).
*Shape.*—Ovate.
*Apex.*—Acute.
*Base.*—Obtuse.
*Margin.*—Mostly entire.
*Length.*—7.0 cm to 12.0 cm.
*Width.*—5.0 cm to 7.0 cm.
*Texture* (*both surfaces*).—Smooth.
*Vein color.*—Upper surface: Transparent. Lower surface: Close to RHS 184D.
*Variegation.*—Absent, but main vein (middle vein) has strong coloration (RHS 184A) secondary vein: RHS 184D, tertiary vein: same color as lower surface of leaves (close to RHS N138B).
*Venation pattern.*—Reticulate.
*Color.*—Mature foliage: Upper surface: between RHS 139A and RHS N189A. Lower surface: close to RHS N138B. Immature foliage: Upper surface: RHS 139A. Lower surface: RHS N138B.
*Leaf petiole.*—Length: 2.0 cm to 3.0 cm. Diameter: 0.2 cm to 0.3 cm. Color: Upper (part) surface: RHS 59A. Lower (part) surface: RHS 59A. Texture: Smooth. Strength: Medium.

Inflorescence:
*Lastingness of inflorescence on the plant.*—4 weeks.
*Natural flowering season.*—End of November.
*Diameter.*—18.0 cm to 21.0 cm.
*Height.*—Approximately 3.0 cm.
*Fragrance.*—Absent.

Bracts:
*Number of bracts per inflorescence.*—12 to 16.
*Shape.*—Ovate.
*Apex.*—Acute.
*Base.*—Obtuse.
*Margin.*—Slightly serrate, young bracts mostly entire.
*Size.*—Length: 4.0 cm to 10.0 cm. Width: 3.0 cm to 7.0 cm.
*Texture* (*both upper and lower surfaces*).—Smooth.
*Venation pattern.*—Reticulate.
*Vein color.*—Upper surface: RHS 184A. Lower surface: RHS 184A.
*Bract color.*—Upper surface: 18-1760 (the Pantone Book of Color; published 1990; page 63; no close color in RHS available) with irregular spots colored RHS NN155A. Lower surface: 18-1760 (the Pantone Book of Color; published 1990; page 63; no close color in RHS available) with irregular spots colored RHS NN155A.
*Bract petiole.*—Length: 0.5 cm to 2.0 cm. Diameter: 0.2 cm to 0.3 cm. Color: Upper (part) surface: RHS 59A. Lower (part) surface: RHS 184A. Texture: Smooth. Strength: Medium.

Cyme:
*Diameter.*—1.5 cm to 3.0 cm.
*Cyathia number per inflorescence.*—7 to 8.
*Deformation of glands of the cyathium.*—Absent.
*Timing of opening of cyathia.*—Opens end of November, duration 1$^{st}$ pollen in parallel to opening of nectar cups, stigma appears 2 weeks later.
*Cyathium.*—Shape: Ovate. Diameter: 0.4 cm to 0.6 cm. Length: 0.5 cm to 0.7 cm. Color: Lower part: RHS 141D. Upper part: 18-1760 (the Pantone Book of Color; published 1990; page 63; no close color in RHS available).
*Peduncle.*—Color: RHS 141D with reddish stripes (close to RHS 184D). Length: 0.2 cm to 0.3 cm. Diameter: 0.1 cm to 0.15 cm. Texture: Smooth. Strength: Medium to strong.
*Nectar cups.*—Number: 1 per cyathium. Diameter: 0.1 cm. Length: 0.4 cm to 0.5 cm. Color: Close to RHS 28A.

Reproductive organs:
*Stamen quantity.*—10 to 20 per cyathium.
*Stamen shape.*—Ovate.
*Filament length.*—0.2 cm.
*Filament color.*—18-1760 (the Pantone Book of Color; published 1990; page 63; no close color in RHS available).
*Pollen quantity.*—Moderate.
*Pollen color.*—Close to RHS 9C.
*Gynoecium.*—Not observed.

Fruit and seed set: Not observed.

COMPARISON WITH PARENTAL LINE AND KNOWN VARIETY

'WEL20390' is distinguished from its mutation parent which is also the closest commercial line as described in Table 1:

TABLE 1

Comparison with Parental and Commercial Line

| Characteristic | Variety 'WEL20390' | Mutation parent 'WEL19375' |
|---|---|---|
| Size of spots | Larger | Smaller |
| Variance of spots | More variance in size | Less variance in size |
| Time of first appearance of spots | Approximately seven days earlier | Approximately seven days later |

COMPARISON WITH SIMILAR VARIETY

Applicant respectfully submits that there are no commercially similar varieties available for comparison other than the female mutation parent.

I claim:

1. A new and distinct variety of poinsettia plant named 'WEL20390' as shown and described herein.

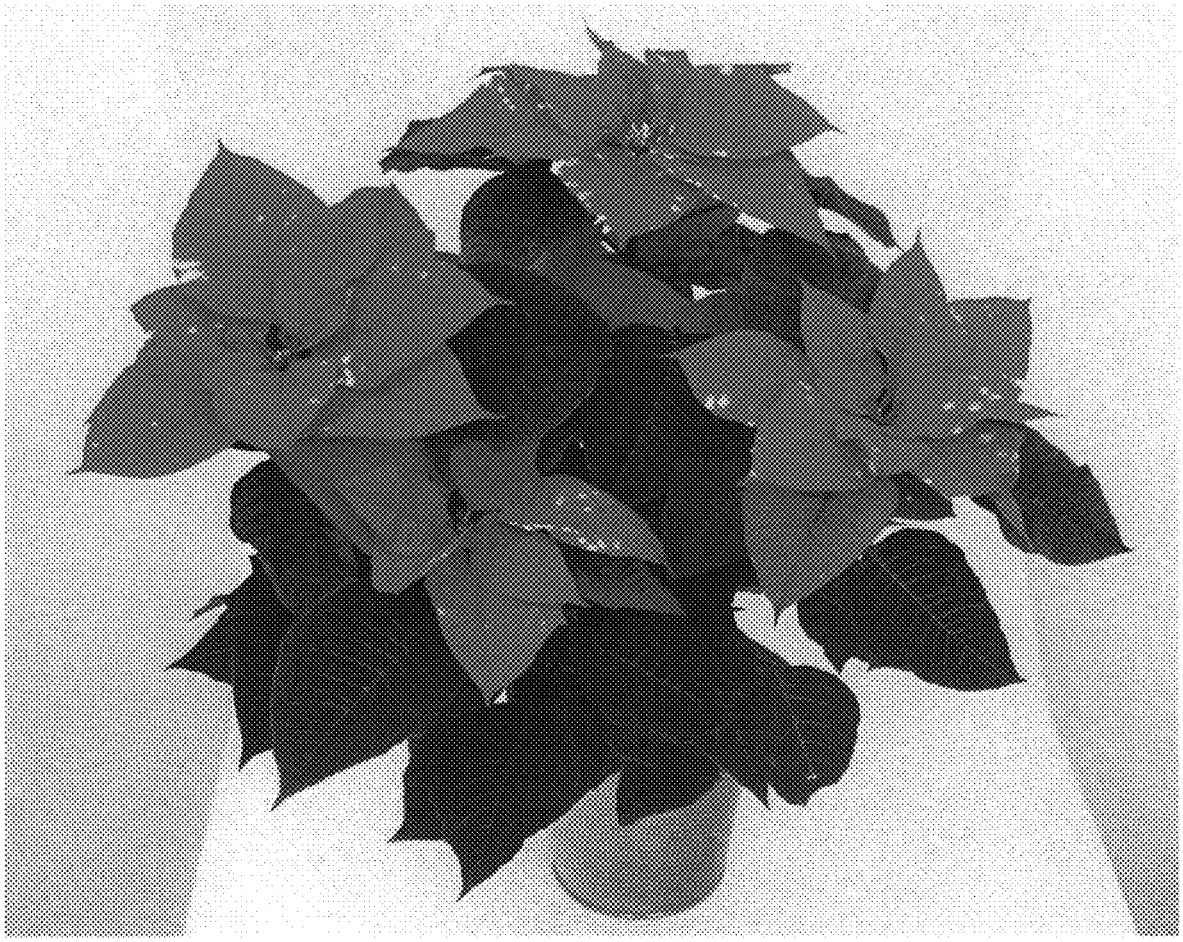

* * * * *